US009851304B2

(12) United States Patent
Fuhr et al.

(10) Patent No.: US 9,851,304 B2
(45) Date of Patent: Dec. 26, 2017

(54) METHOD AND DEVICE FOR MONITORING A CRYOPRESERVED BIOLOGICAL SAMPLE

(75) Inventors: Guenter R. Fuhr, Berlin (DE); Heiko Zimmermann, Frankfurt am Main (DE); Frank Stracke, Saarbruecken (DE); Daniel Doerr, Heusweiler (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 13/988,558

(22) PCT Filed: Oct. 26, 2011

(86) PCT No.: PCT/EP2011/005401
§ 371 (c)(1),
(2), (4) Date: May 31, 2013

(87) PCT Pub. No.: WO2012/069117
PCT Pub. Date: May 31, 2012

(65) Prior Publication Data
US 2013/0244271 A1     Sep. 19, 2013

(30) Foreign Application Priority Data

Nov. 24, 2010  (DE) .................. 10 2010 052 434

(51) Int. Cl.
*G01N 21/65*     (2006.01)
(52) U.S. Cl.
CPC ........... *G01N 21/65* (2013.01); *G01N 21/658* (2013.01)
(58) Field of Classification Search
CPC .......................... G01N 21/65; G01N 21/658
See application file for complete search history.

(56) References Cited

U.S. PATENT DOCUMENTS

| 4,823,166 A | 4/1989 | Hartog et al. |
| 5,084,377 A | 1/1992 | Rowan et al. |
| 2004/0073120 A1 | 4/2004 | Motz et al. |
| 2006/0082762 A1 | 4/2006 | Leverette et al. |
| 2006/0139633 A1 | 6/2006 | Puppels et al. |
| 2006/0155195 A1 | 7/2006 | Maier et al. |
| 2008/0306346 A1 | 12/2008 | Claus et al. |

FOREIGN PATENT DOCUMENTS

| DE | 3687438 T2 | 5/1993 |
| DE | 10123443 A1 | 11/2002 |
| DE | 60314282 T2 | 3/2008 |
| EP | 1438421 B1 | 7/2009 |
| WO | 2006058816 A1 | 6/2006 |
| WO | 2007080442 A2 | 7/2007 |

OTHER PUBLICATIONS

Dong et al., Spatial Distribution of the State of Water in Frozen Mammalian Cells, Biophysics Journal, vol. 99, Oct. 2010, 2453-2459.*
Toptica, High-resolution Raman microscopy, 2007.*
Doerr et al., Multiphoton microscopy for the in-situ investigation of cellular processes and integrity in cryopreservation, Biotechnol. J, 2009, 4, 1215-1221.*
Janus, Application Systems, Web page, Nov. 21, 2010.*
Tiwari et al., Fiber optic Raman sensor to monitor the concentration ratio of nitrogen and oxygen in a cryogenic mixture, Jun. 1, 2007_vol. 46, No. 16_Applied Optics.*
Badii et al., "Effect of Antioxidants, Citrate, and Cryoprotectants on Protein Denaturation and Texture of Frozen Cod (*Gadus morhua*)", J. Agric. Food Chem, vol. 50, pp. 2053-2061 (2002).
Hawke et al., "An apparatus for high pressure Raman spectroscopy", Rev. Sci. Instrum., vol. 45, No. 12, pp. 1598-1601 (1974).
Ike et al., "Crystallization and vitrification of cryoprotectants studied by Raman scattering, Brillouin scattering and THz-TDS", Journal of Molecular Structure, vol. 924-926, pp. 127-130 (2009).
Terada et al., "Application of "in vivo cryotechnique" to detect erythrocyte oxygen saturation in frozen mouse tissues with confocal Raman cryomicroscopy", Journal of Structural Biology, vol. 163, pp. 147-154 (2008).
Tulk et al., "Hydrogen bonding in glassy liquid water from Raman spectroscopic studies", Journal of Chemical Physics, vol. 109, No. 19, pp. 8478-8484 (1998).
International Search Report for PCT/EP2011/005401 dated Feb. 2, 2012.
Hashimoto et al. (2008). Application of cryoprotective ethylene glycol solutions to protein crystals. Cryobiology and Cryotechnology, 54(2): 119-122.
Partial English Translation of Hashimoto et al. (2008). Application of cryoprotective ethylene glycol solutions to protein crystals. Cryobiology and Cryotechnology, 54(2): 119-122.

* cited by examiner

*Primary Examiner* — Taeyoon Kim
*Assistant Examiner* — Srikanth Patury
(74) *Attorney, Agent, or Firm* — Caesar Rivise, PC

(57) ABSTRACT

The invention relates to a method for monitoring a cryopreserved biological sample (1), comprising the steps of providing the biological sample (1) in a cryopreserved state, measuring at least one Raman spectroscopic sample characteristic by means of a Raman spectroscopic measuring apparatus (10, 20), comparing the at least one sample characteristic with a reference characteristic by means of an evaluating apparatus (30), and providing a state characteristic that depends on the result of the comparison and that is characteristic of a storage state of the biological sample (1). The invention further relates to a monitoring device for cryopreserved samples, in particular for performing said method.

19 Claims, 2 Drawing Sheets

METHOD AND DEVICE FOR MONITORING A CRYOPRESERVED BIOLOGICAL SAMPLE

BACKGROUND OF THE INVENTION

The invention relates to a method for monitoring a cryopreserved biological sample, in particular a method for controlling the state of a cryopreserved biological sample. Furthermore, the invention relates to a monitoring device, which is configured for monitoring a cryopreserved biological sample, in particular according to the said method. Applications of the invention are given in the state and quality control of cryopreserved samples, in particular in long-term storage (e.g. in banks with biological samples) or in the clinical sample control.

Cryopreservation is the only known technology, which has proven suitable for a life-sustaining and/or function-preserving long-term storage or archiving of biological samples, such as biological cells (including gametes), cell constituents, cell compositions, tissues or tissue parts, under practical conditions. Based on the most recent development in the reproductive and regenerative medicine, in the so-called "Tissue Engineering" and in cellular biology (in particular stem cell biology) and due to new applications of cryopreservation, for example in the protection of species, a strong demand exists for massive-scale storage of biological samples in the cryopreserved state.

One important requirement towards cryopreservation of biological samples consists in the fact that the samples are to be stored free of damages. The application of biological samples after cryopreservation, for example during implantation of living biological cells into an organism, can result in dramatic sanitary consequences for the organism in case the samples have suffered for example genetic, epigenetic or functional damage during cryopreservation. Damages can occur in particular through changes in the sample constituents, such as aqueous sample constituents, during cooling down or thawing of the sample. Whilst the steps of cooling down or of thawing of the biological samples are examined for possible damaging potentials and optimized for the practical application, experiences on possible changes of the samples in the cryopreserved state have been only limitedly available to date. Checking the sample quality is at this point in time possible only by partial or complete thawing of the sample. Interim thawing of a cryopreserved sample, however, increases the risk of damage.

To date, it is assumed that below the glass transition temperature of water at −137° C. any chemical conversion is slowed down in a practically infinite manner and that no recrystallization effect can occur in this temperature range of water. Therefore, a sample, which was led damage-free in the temperature range below −130° C. is considered stably preserved. This assumptions are made in particular for the vitrification of biological samples, wherein the sample is frozen with such high cooling rate that no damaging ice crystals can be formed.

It is known from the practice, however, that, even if the formation of ice crystals is avoided during cooling down or thawing, the samples can exhibit damages after the thawing. To date, however, monitoring of the state or the quality of long-term stored samples does not take place. Even if there is the option of taking a partial sample from a diversity of samples and, after their thawing, analyzing their state, it is, however, not possible to draw conclusions from a partial sample for other partial samples or for the bulk sample due to the statistical nature of the damaging processes that take place. Reliable technical solutions for monitoring the state of the samples in situ, thus in the deep-cold state, are not available to date.

WO 2006/058816 discloses a sample container for a cryopreserved sample, wherein an optical analysis of the sample is provided for in the sample container. It is suggested to detect recrystallization processes through reflexion measurements or transmission measurements. The measurements are, however, not suitable for a quantitative sample characterization. They are only limitedly applicable even for qualitative observations, since the measured light intensities not only depend on a possible sample-recrystallization, but also sensitively on other effects. It is furthermore suggested that the sample is provided with a fluorescence marker (fluorescence staining), in order to monitor the formation of extra-cellular ice, wherein, however, no statement is made on the detection of a crystallization state of the sample.

A further sensitive method of analysis is the generally known Raman spectroscopy. This method is, for example, mentioned in US 2006/0082762 A1 or by R. S. Hawke et al. (in "Rev. Sci. Instr." Vol. 45, 1974, p. 1598 ff.) without, however, addressing the measurement on biological samples. It is suggested in US 2004/0073120 A1 to perform Raman spectroscopic measurements on biological tissue samples. The measurements can, however, only be performed on samples at room temperature. Raman spectroscopic measurements on biological samples at room temperature are also mentioned in EP 1 438 421 B1, DE 101 23 443 A1, DE 36 87 438 T2, US 2008/0306346 A1 and US 2006/0155195 A1.

It is known from the publication of C. A. Tulk et al. in "Journal of Chemical Physics" (Vol. 109, 1998, p. 8478) to characterize differences of the chemical linkage in amorphous ice and crystalline ice through Raman spectroscopic measurements. Application of these measurements, which were performed with specialized spectroscopic apparatuses for the fundamental research, are not mentioned by C. A. Tulk et al.

The objective of the invention is to provide an improved method for monitoring a cryopreserved biological sample by means of which disadvantages of conventional techniques are overcome. The monitoring method should in particular allow sample observation without any change on the sample and/or gaining of quantitative information about the crystallization state (in particular the degree of crystallization) and/or about chemical changes in the sample with improved reliability and/or accuracy. The objective of the invention is furthermore to provide an improved device for monitoring a cryopreserved biological sample by means of which disadvantages of conventional techniques are overcome. The monitoring apparatus should in particular be compatible with available techniques for cryopreservation of biological samples.

These objectives are achieved by a method and a device, respectively, of the invention.

DESCRIPTION OF THE INVENTION

According to a first aspect of the invention, said objective is generally achieved by a method for monitoring a cryopreserved biological sample, wherein a Raman spectroscopic measurement is performed on the biological sample in the cryopreserved state. According to the invention it is envisaged to provide the biological sample in the cryopreserved state in a storage area of a cryopreservation device, such as e.g. a tank, in which a temperature below the freezing point of water prevails, in particular the temperature of the liquid nitrogen or of the vapour above the liquid nitrogen. According to the invention, it is furthermore envisaged to measure at least one Raman spectroscopic sample characteristic on the biological sample, which characteristic will be compared with at least one reference characteristic. According to the invention, it is furthermore envisaged to provide a state characteristic, which depends on the result of the comparison and is characteristic for a storage condition of the biological sample.

It has been ascertained with the invention that the application of the Raman spectroscopic measurement provides at least one sample characteristic, which, through the comparison with the reference characteristic, advantageously allows an immediate statement about the crystallization state and the chemical composition of the sample. Differing from the conventional reflexion or transmission measurement, which is based on the outer appearance of the sample (clear, diffuse, finely or coarsely crystalline, non-uniform), the Raman spectroscopic measurement represents a physical approach by means of which molecular properties of the sample and/or of the sample container are determined. Undesirable effects on the measurement result, for example by a foggy sample container, are excluded. In particular chemical processes on main constituents of the sample, such as on cryoadditives (like dimethyl sulfoxide, glycerine, ethylene glycol and trehalose) and on the biological material itself can be detected and optionally quantified. Advantageously, the method can be performed on a cryopreserved sample, which is free of targetedly supplied marker substances for spectroscopic measurements. Furthermore, the invention allows that, in addition to the crystallization state, further properties of the sample, such as chemical transformations of sample constituents, are recorded.

According to a second aspect of the invention, said objective is generally achieved by a monitoring apparatus, which is configured for monitoring a cryopreserved biological sample by means of a Raman spectroscopic measurement. The monitoring apparatus according to the invention comprises a Raman spectroscopic measuring device, with which the at least one Raman spectroscopic sample characteristic can be measured. The Raman spectroscopic measuring device generally comprises a illuminating device for illuminating the sample and/or the sample container, preferably a light-emitting diode or a laser, and a detector device for detection of light, which is scattered in an inelastic manner from the sample and/or the sample container. The Raman spectroscopic measuring device can be structured like a conventional Raman-spectrometer or specially adapted to the measurement conditions when monitoring the sample. The monitoring apparatus according to the invention furthermore comprises one evaluation device. The evaluation device, which comprises for example at least one computing device, is configured for two functions, which comprise a comparison of the at least one measured Raman spectroscopic sample characteristic with a reference characteristic and providing a state characteristic, which depends on the result of the comparison and is characteristic for a storage condition of the biological sample.

One important advantage of the invention consists in the fact that, differing from all conventional applications of the Raman spectroscopy, in particular a trouble-free and damage-free in-situ-monitoring of biological samples during storage under low temperature conditions, for example at −136° C. or below, is allowed.

Advantageously, the monitoring apparatus is suitable for a contactless characterization of the sample. It is not necessary to take out the sample prior to, during or following the measurement from a storage area of the cryopreservation device, or to bring the sample back into it. Preferably, the sample would leave the measurement the storage area with the low temperature conditions at no point in time, i.e. there is no interruption of the cooling chain. The storage area, in particular a sample container, remains closed. The measurement can be performed contactless through an optical interface in the storage area.

The invention allows in particular monitoring under low temperature conditions by performing measurements repeatedly, for example on a monthly or yearly basis. The inventors have found that the physical-chemical processes, such as phase transformations, phase separations and/or crystallization processes, can be characterized under low temperature conditions with a Raman spectroscopic measurement.

The term of "Raman spectroscopic measurement" designates any optical measurement, which allows for the quantitative or qualitative detection of inelastic scattering (Raman line) in the material of the sample, in particular in a frozen aqueous constituent of the sample, and/or of the sample container when irradiating with at least one wavelength in the UV, VIS and/or IR range. In particular, the intensity, the spectral position, the occurrence and/or the temporal development of at least one Raman line is/are detected. A "Raman spectroscopic sample characteristic" is the result of the Raman spectroscopic measurement.

According to a first advantageous variant of the invention, the Raman spectroscopic measurement comprises the measurement of a complete Raman spectrum or at least a section of a Raman spectrum of at least one portion of the sample and/or of the sample container. In this case, the Raman spectroscopic sample characteristic has a high information content, which, in addition to the detection of the degree of crystallization, also allows for characterization of the chemical composition of the sample. According to a second advantageous variant of the invention, the Raman spectroscopic measurement comprises the measurement of at least one spectral emission value of a Raman spectrum of at least one portion of the sample and/or of the sample container. In this case, advantages can result for a simplified structure and compactness of the monitoring apparatus. According to a further advantageous variant, a time resolved Raman spectroscopic measurement can be provided for on at least one portion of the sample and/or of the sample container. Said variants can be combined permanently or for certain periods of time during implementation of the invention.

According to a preferred embodiment of the invention, the Raman spectroscopic measurement takes place directly on the biological sample in the cryopreserved state, i.e. on the frozen sample, in particular with a temperature below 0° C. The temperature of the cryopreserved sample is selected in a specific case depending on the concrete preservation task and is preferably less than −80° C., in particular for slightly sensitive, e.g. slowly frozen samples, in particular less than −136° C., in particular for glassily frozen and/or very sensitive samples.

According to a further embodiment of the invention, the Raman spectroscopic measurement can alternatively or additionally take place on the wall material of a sample container, which contains the cryopreserved sample. Advantageously, undesirable changes of the sample, e.g. chemical transformations or geometric changes due to recrystallization processes, and/or of the storage conditions, e.g. undesirable temperature fluctuations, can have an impact on the intensity, the spectral position, the occurrence and/or the temporal decay behaviour of at least one Raman line of the material of the sample container. The measurement on the wall material of a sample container can, for example, comprise monitoring of the container materials polyethylene and polypropylene. Both substances are semi-crystalline (and therefore optical turbid). They remain amorphous (and then also clear) only with the addition of plasticizers (e.g. terephtalate). A (continuous) change of the crystalline moiety at low temperatures, along with embrittlement of the material, can be determined according to the invention.

According to a further embodiment of the invention, the Raman spectroscopic measurement can alternatively or additionally take place on a probe substance included in the biological sample. For example, metal colloids (preferably such of gold and silver) can be used as the probe substance, which metal colloids can lead through the Surface Enhanced Raman Scattering (SERS) effect to a considerable amplification of individual vibration bands and thus also special constituents of the sample. Furthermore, additives showing e.g. a compound formation with water in the solid phase (including also the cryoprotectants DMSO and ethylene glycol) as well as concentration-dependent chemical transformations (e.g. dimeric equilibrium, crystallizing-out) can be used for Raman spectroscopic sample characterization.

The term "reference characteristic" designates any physical, in particular spectroscopic quantity, which is suitable for characterization of a temporally stable, chemically and/or physically non-changing measurement object. The reference characteristic can, for example, comprise a saved table value, which is known from previous comparative measurements or theoretical simulations. The reference characteristic can furthermore comprise a spectral reference value within the sample characteristic, such as the amplitude of a predetermined Raman line in the Raman spectrum. In this way, an internal reference is advantageously provided. An internal reference can furthermore be formed by a predetermined combination of at least two characteristics of the measured Raman spectrum, such as a predetermined ratio of amplitudes of Raman lines. The reference characteristic can alternatively or additionally comprise a sample characteristic measured at a previous point in time, such as a Raman spectrum, so that a temporal reference is advantageously provided. In this regard, the Raman spectroscopic measurement is repeated in predetermined time intervals, such as on a daily, weekly or monthly basis. Preferably, the evaluation device of the monitoring apparatus correspondingly comprises a memory, which is set up for storing the reference characteristic.

Advantageously, there are different options for the comparison of the at least one Raman spectroscopic sample characteristic with the at least one reference characteristic. For example, a substraction (such as amplitude or spectral position) can be provided for between each measured sample characteristic and the reference characteristic. In this case, the evaluation of the measurement can be simplified. The substraction can in particular comprise a detection of the shift of the spectral position of individual bands. A ratio formation (quotient formation) can alternatively or additionally be provided for between the sample characteristic and the reference characteristic. In this case, advantages can result for an enhanced sensitivity of the measurement. Preferably, the evaluation device of the monitoring apparatus correspondingly comprises a subtraction and/or a dividing unit.

The term "state characteristic" designates any physical quantity or any object that can be presented as information and which unambiguously characterizes the physical and/or chemical state of the sample and/or of the sample container, in particular the crystallization state of the sample. For example, generating an information, which refers to the state, the quality and a contamination of the biological sample can be envisaged for providing the state characteristic. Preferably, a text information, with which said properties of the sample are designated, such as "starting crystallization", "homogeneous distribution of the cryoprotectant" or "negligible solvent contamination" is displayed or otherwise indicated. A quantitative value, which is characteristic for a moiety of frozen water in the amorphous state and/or a moiety of frozen water in the crystalline state (degree of crystallization) can alternatively or additionally be directly output. A quantitative value, which is characteristic for a change of non-aqueous constituents of the sample and/or of the sample container can alternatively or additionally be directly output. The term state characteristic also includes signals, such as visual or acoustic signals, which indicate a specific sample state. For example, an alarm signal can be generated, which indicates a characteristic change of the biological sample, and/or a degradation signal can be generated by means of which the destruction of the biological sample is signalized. Preferably, the evaluation device of the monitoring apparatus correspondingly comprises an output device, which is set up for output of the state characteristic and/or an indicator and/or alarm device, with which characteristic states of the biological sample can be indicated.

One important advantage the invention consists in the fact that, during the Raman spectroscopic measurement and the subsequent steps, including the provision of the state characteristic of the sample, the biological sample can remain in the cryopreserved state, in particular in the environment provided for and suitable for cryopreservation. This concerns in particular amorphously solidified, aqueous samples, whose temperature is permanently maintained below −136° C. Preferably, the Raman spectroscopic measuring device and the evaluation device are operated spatially and thermally decoupled from the sample arranged in a cooled storage area. The signals provided for the Raman spectroscopic measurement (light for illuminating, information-bearing, detected Raman-scattered light) are transmitted optically between the storage area and the measurement and evaluation device, preferably via a window- or light guide optics.

A further independent subject of the invention is the use of a Raman spectroscopic measurement for monitoring the state of a cryopreserved biological sample in a cryopreservation device, in particular in a sample receptacle in a cryotank.

BRIEF DESCRIPTION OF THE DRAWINGS

Further details and advantages of the invention will be described below with reference to the attached drawings. The figures show as follows.

Preferred embodiments of the invention will be described below with reference to the features of the combination of a Raman spectroscopic measuring device with a cryopreserved biological sample. Details of the Raman spectroscopic measurement and in particular of the illuminating and detector device provided for this are not described, since the Raman spectroscopy as such is known from the prior art. Reference is made by way of example to the measurement of the Raman scattering in the biological sample, wherein the monitoring system according to the invention can accordingly be based on the measurement of the Raman scattering in the material of the sample container. The invention can be used in monitoring of samples, which are provided in cryopreservation devices and according to cryopreservation methods as is known per se. Therefore, details of the cryopreservation technique are not described here as well.

Figure 1:
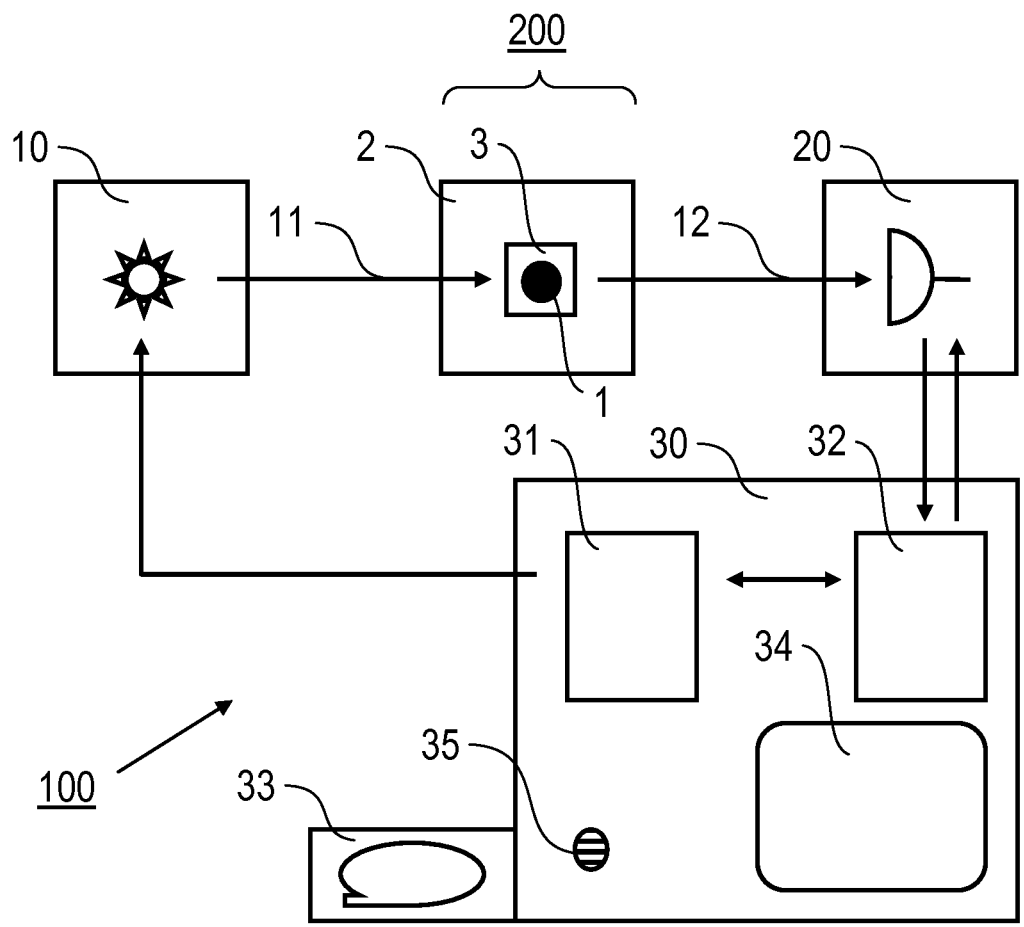
FIG. 1: a schematic illustration of features of preferred embodiments of the invention.

FIG. 1 shows in a schematic view the combination of the monitoring apparatus 100 according to the invention with a cryopreservation device 200. The monitoring apparatus 100 comprises the Raman spectroscopic measuring device with the illuminating device 10 and the detector device 20 and the evaluation device 30, which is connected with the detector device 20 and, optionally, also with the illuminating device 10 for data or signal transmission. The cryopreservation device 200 comprises at least one biological sample 1 in a sample container 3, which is arranged in a cooling device 2. Differing from the schematic illustration in FIG. 1, a plurality of sample containers 3 are in practice provided each with one or more biological samples 1 in a cooling device 2. The cooling device 2 is, for example, a cryotank cooled with liquid nitrogen.

The illuminating device 10 comprises as a light source for exciting the Raman scattering in the biological sample 1 or the material of the sample container 3 a laser, such as a solid laser with an emission wavelength $\lambda=532$ nm or a narrow band diode laser with an emission wavelength $\lambda=785$ nm. The detector device 20 is configured for the detection of light scattered in the sample 1 or the material of the sample container and for the measurement of at least one Raman spectroscopic sample characteristic. The detector device 20 comprises a wavelength-selective element and a light-sensitive element, such as a photodiode or a CCD camera. The wavelength-selective element comprises, depending on the Raman spectroscopic sample characteristic to be measured concretely, for example, a monochromator or at least one optical filter.

The evaluation device 30 comprises a memory 31 for storing a reference characteristic for the evaluation of the Raman spectroscopic sample characteristic, a computing device, in particular a comparator device 32, which is adapted for a comparison of the measured Raman spectroscopic sample characteristic with the reference characteristic and, for example, contains a subtraction unit and/or a dividing unit. Furthermore, the evaluation device 30 is equipped with an output device 33, such as a printer, a display device 34, such as a display screen, and an alarm device 35, such as an acoustic alarm. The evaluation device 30 can, for example, be formed by a computer, which contains the components 31, 32, 34 and 35 and is additionally connected with the component 33. The evaluation device 30 can be integrated into a control device of the cryopreservation device 200.

The evaluation device 30 is connected with the detector device 20. A transmission of measurement signals from the detector device 20 to the evaluation device 30 is provided for. Furthermore, the transmission of control signals from the evaluation device 30 to the detector device 20 can be provided for operation of the detector device. For example, control signals can be provided for setting of the wavelength-sensitive element of the detector device 20. Optionally, a connection is furthermore provided for between the evaluation device 30 and the illuminating device 10, for example, in order to switch the illuminating device 10 and/or set up a predetermined wavelength for excitation of the Raman scattering, depending on the actual operating state of the monitoring apparatus 100.

The illuminating device 10 is optically coupled with the sample 1 via an illuminating optics 11. The illuminating optics 11 comprises, for example, a free space optics or a light guide optics. In the case of the free space optics, excitation light is directed from the illuminating device 10, if applicable via optical refractive and/or reflective elements and through a window in a wall of the cooling device 2 to the sample container 3. If the wall material of the sample container 3 is transparent for the wavelength of the excitation light of the illuminating device 10, the excitation light directly impinges the sample 1. Otherwise, a window can be provided for in the wall material of the sample container 3, respectively, for coupling-in of the excitation light. If the illuminating optics 11 comprises a light guide optics, a light guide is provided for from the illuminating device 10 into the cooling device 2 to the sample container 3, where the excitation light from the light guide is coupled in through the wall material of the sample container 3 or a corresponding optical window to the biological sample 1. Furthermore, the biological sample 1 is optically connected via a detector optics 12 with the detector device 20. The detector optics 12 comprises a window- or light guide optics, as has been described above with reference to the illuminating optics 11.

The geometry of the Raman spectroscopic measurement can be freely selected depending on the concrete monitoring task and the geometric conditions in the cryopreservation device 200. Differing from the variant schematically illustrated in FIG. 1 with separated illuminating and detector optics 11, 12, both light paths can entirely or partially fall together.

For carrying out the method according to the invention with monitoring of a biological sample, the sample 1 is provided in the cryopreserved state in the cryopreservation device 200. The illuminating device 10 and the detector device 20 are used to perform the measurement of at least one Raman spectroscopic sample characteristic, such as of a Raman spectrum of aqueous sample constituents. The Raman spectrum is transmitted to the evaluation device 30 and subjected in the comparison device 32 to a comparison with at least one reference characteristic. The reference characteristic comprises, for example, a comparison spectrum, which is saved in the memory 31. If specific Raman lines show any characteristic variation in the measured Raman spectrum, a state characteristic is output or displayed with at least one of the components 33, 34 and 35. For example, if the intensity of a predetermined Raman line, which, if necessary, is normalized relative to a further line in the spectrum, exceeds a predetermined threshold value (reference characteristic), a text information such as "degree of crystallization at least 10%" is output on the display device 34 or with the printer 33 or, in the case of critical states of the sample, for example, an alarm signal can sound.

Figure 2:
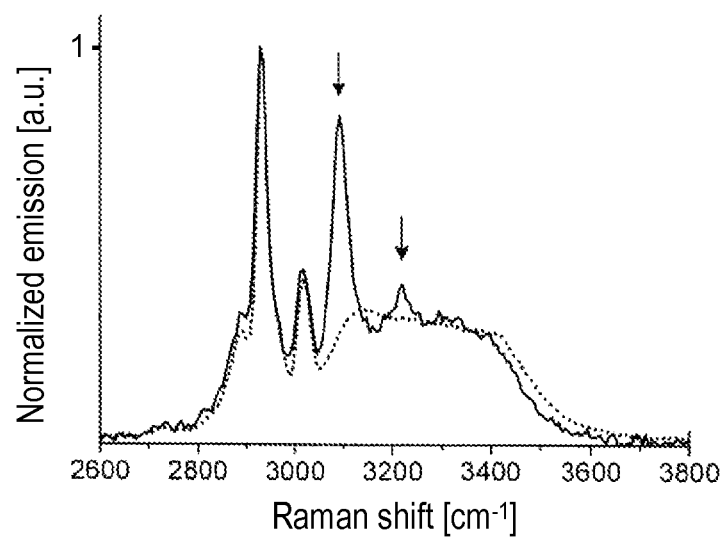
FIGS. 2 and 3: curve illustrations, which show experimental results during application of the method according to the invention.
Figure 3:
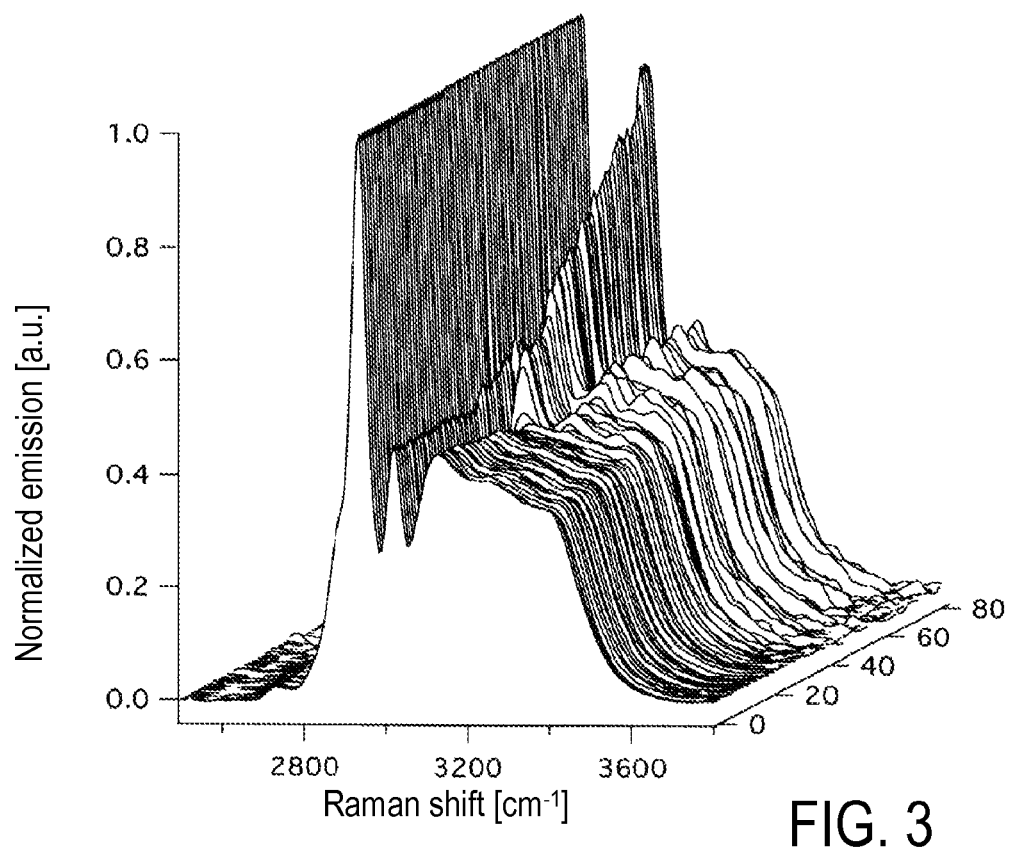

Experimental results on which the determination of a state characteristic can be based are illustrated by way of example in FIGS. 2 and 3. The results were measured on model systems, such as on a solution of the cryoprotectant DMSO (dimethyl sulfoxide).

FIG. 2 illustrates by way of example Raman spectra of an aqueous 20% DMSO solution with 20% of ethylene glycol, which was vitrified (glassily frozen) by dropping onto a cooling block with a temperature of $-196°$ C. and then heated up in a controlled manner. The dotted curve shows the Raman spectrum of the vitrified water having the unstructured emission which is typical for liquid water. Following a crystallization of the sample to crystalline ice, wherein the glass transition temperature of the sample is exceeded, sharp bands (see arrows), which are characteristic for the Raman scattering on crystalline water, become visible in the Raman spectrum. The additional bands at 2920 $cm^{-1}$ and 3020-$cm^{-1}$, which are caused by the CH stretching vibration of the DMSO, can be used as an internal reference or for normalization of the lines of the crystalline ice. The spectra shown in FIG. 2 can directly be used for formation of the sample characteristic to be measured according to the invention. The sample characteristic can, for example, comprise the sharp Raman lines of the crystalline water and/or the fine structure of the Raman spectrum in the long-wavelength range. Accordingly, the bands lines of completely crystallized water can likewise be used as the reference characteristic or the lines of the DMSO constituents can be used as benchmark. A further experimental result based on which the monitoring of cryopreserved biological samples according to the invention can be performed is illustrated in FIG. 3. FIG. 3 shows a time series of Raman spectra of a DMSO solution at 20% that has initially been vitrified. The begin of the formation of crystalline ice and the progress of the formation of the crystallized ice are made clearly visible by the appearance of corresponding crystal ice lines.

Further examples for the Raman spectroscopic monitoring of changes in state in cryopreserved samples can be given by other phase transformations in the medium of the sample. Through addition of a cryoprotectant, a sample often targetedly solidifies in metastable states. During the time of storage of the cryopreservation, however, phase transformations such as segregations of constituents, crystallizing-out of cryoprotectants or the like can occur. Such phase transformations are also made visible with samples and/or cryoprotectants with a complex composition on the Raman spectrum.

Further examples for the Raman spectroscopic monitoring of changes in state in cryopreserved samples are based on the phenomenological tracking of slow (i.e. not abrupt) changes of the chemical composition of the sample. Based on the saved Raman spectra from the time point following directly the initial cooling of the sample, chemical changes in the sample can be detected through comparison of Raman spectra measured later with the saved spectra. Since the cryopreservation is based on the infinite deceleration of (bio)chemical processes, each change of the spectra and thus each chemical reaction in the sample can be used as an indication of a change in state. The main constituents of the preserved organisms (lipids, proteins, nucleic acids) can, here, be targetedly observed by means of their characteristic Raman lines (P=O, P—O, C=O, C—H, N—H).

A further option consists in the monitoring of the material of the sample container, which often contains a plastic, in particular a polymer material. A change of the spectra of the material of the sample container can allow for conclusion of chemical ageing effects, which are used as an indication of a parallel change in state in the sample or which, if applicable, jeopardize the sterility of the sample during the storage time or, however, at the latest during thawing. Ageing effects in the material of the sample container can comprise e.g. a formation of semi-crystalline ranges, which are indicative of embrittlement of the wall of the sample container.

The features of the invention disclosed in the previous description, the drawings and the claims can be significant individually as well as in combination for the realization of the invention in its different embodiments.

The invention claimed is:

1. A method for monitoring a cryopreserved biological sample, comprising the steps of:
   (A) providing the biological sample in a cryopreserved state in a sample container arranged in a storage area of a cryopreservation device, wherein the storage area is maintained at a cryopreservation temperature,
   (B) measuring at least one Raman spectroscopic sample characteristic on the biological sample in the cryopreserved state, wherein the step of measuring the at least one Raman spectroscopic sample characteristic is performed on the biological sample in the storage area of the cryopreservation device using a Raman spectroscopic measuring device, which comprises: (i) an illuminating device that illuminates the sample and the sample container, (ii) a detector device that detects light, which is scattered in an inelastic manner from the sample and the sample container, and (iii) light guide optics running from a position inside the storage area to the detector device outside the storage area, wherein signals for measuring the at least one Raman spectroscopic sample characteristic are transmitted optically through the light guide optics from the storage area to the detector device,
   (C) comparing the at least one sample characteristic with a reference characteristic, and
   (D) providing a state characteristic, which depends on the result of the comparing step (C) and is characteristic for a storage condition of the biological sample.

2. The method according to claim 1, in which the measuring step (B) comprises:
   measuring a complete Raman spectrum or at least one section of a Raman spectrum of at least one portion of the sample.

3. The method according to claim 1, in which the measuring step (B) comprises:
   measuring at least one spectral emission value of a Raman spectrum of at least one portion of the sample.

4. The method according to claim 1, in which the measuring step (B) comprises:
   Raman spectroscopic measurement of a temporal development of the at least one Raman spectroscopic sample characteristic on at least one portion of the sample.

5. The method according to claim 1, in which
   the measuring step (B) takes place on at least one of the biological sample, a probe substance contained in the biological sample and the sample container.

6. The method according to claim 1, in which
   the reference characteristic comprises at least one of a saved table value, a spectral reference within the sample characteristic and a sample characteristic measured at a prior point in time.

7. The method according to claim 1, in which the comparing step (C) comprises:
   providing a difference between the sample characteristic and the reference characteristic.

8. The method according to claim 1, in which the comparing step (C) comprises:
   providing a ratio of the sample characteristic and the reference characteristic.

9. The method according to claim 1, in which providing the state characteristic in step (D) comprises:
   generating an information, which refers to at least one of a state, a quality and a contamination of the biological sample.

10. The method according to claim 1, in which providing the state characteristic in step (D) comprises:

output of a quantitative value, which is characteristic for at least one of a percentage of frozen water in an amorphous state and a percentage of frozen water in a crystalline state.

11. The method according to claim 1, in which providing the state characteristic in step (D) comprises:
output of a quantitative value, which is characteristic for at least one of a change of non-aqueous constituents of the sample and of a sample container.

12. The method according to claim 1, in which providing the state characteristic in step (D) comprises:
generating an alarm signal, which indicates a characteristic change of the biological sample.

13. The method according to claim 1, in which providing the state characteristic in step (D) comprises:
generating a degradation signal, which indicates a destruction of the biological sample.

14. The method according to claim 1, in which
the Raman spectroscopic measuring device, and an evaluation device, which compares the at least one measured Raman spectroscopic sample characteristic with a reference characteristic and provides the state characteristic, are operated thermally decoupled from the sample.

15. The method according to claim 1, in which the measuring step (B) comprises illuminating
the biological sample via light guide optics.

16. The method according to claim 1, in which the measuring step (B) comprises illuminating
the biological sample with a spectral narrow band light source.

17. The method according to claim 1, in which the measuring step (B) is repeated at
predetermined time intervals.

18. The method according to claim 1, in which the measuring step (B) comprises keeping
of the biological sample during the measurement in an environment that is suitable for cryopreservation.

19. The method of claim 16, wherein the light source comprises a light-emitting diode or a laser.

* * * * *